United States Patent [19]

Chang et al.

[11] 4,106,939

[45] Aug. 15, 1978

[54] IMAGING AND RECORDING OF INFORMATION UTILIZING A TELLURIUM TETRAHALIDE COMPLEX OF AN AROMATIC AMINE

[75] Inventors: Yew C. Chang, Oakville, Canada; Stanford R. Ovshinsky, Bloomfield Hills; David A. Strand, Novi, both of Mich.

[73] Assignee: Energy Conversion Devices, Inc., Troy, Mich.

[21] Appl. No.: 838,574

[22] Filed: Oct. 3, 1977

Related U.S. Application Data

[63] Continuation-in-part of Ser. No. 596,617, Jul. 17, 1975, abandoned, which is a continuation-in-part of Ser. No. 384,089, Jul. 30, 1973, abandoned.

[30] Foreign Application Priority Data

Jul. 17, 1974 [GB] United Kingdom .............. 31676/74

[51] Int. Cl.$^2$ .......................... G03C 5/24; G03C 1/00
[52] U.S. Cl. .................... 96/48 R; 96/48 HD; 96/27 R; 96/88; 427/43; 428/411; 428/913; 204/2; 346/1; 346/135
[58] Field of Search .................. 428/411, 913; 96/88, 96/48 R, 48 HD, 27 R; 427/43; 204/2; 346/1, 135

[56] References Cited

U.S. PATENT DOCUMENTS

| | | | |
|---|---|---|---|
| 3,147,117 | 9/1964 | Wainer et al. | 96/48 R |
| 3,527,639 | 9/1970 | Moraw | 96/90 R |
| 3,579,342 | 5/1971 | Strilko | 96/90 R |
| 3,700,448 | 10/1972 | Hillson et al. | 96/88 |
| 3,813,245 | 5/1974 | Laridon et al. | 96/90 R |
| 3,819,377 | 6/1974 | Klose et al. | 96/48 HD |
| 3,887,374 | 6/1975 | Brougo et al. | 96/90 R |

OTHER PUBLICATIONS

Boudreaux, J. Amer. Chem. Soc., vol. 85, No. 14 (1963), pp. 2039–2043.
Boudreaux, J. Amer. Chem. Soc., vol. 80, (1957), pp. 1588–1590.
Morgan, J. Chem. Soc., (1929), pp. 1103–1111.
Ryabchikov, Russian Chem. Reviews (1964), pp. 55–64.

*Primary Examiner*—Won H. Louie, Jr.
*Attorney, Agent, or Firm*—Wallenstein, Spangenberg, Hattis & Strampel

[57] ABSTRACT

Selected areas of a layer comprising an imaging material in the form of a tellurium tetrahalide adduct of an aromatic amine, exemplified by a tellurium tetrachloride adduct of dimethyl aniline, which adduct is free from any diazo groups, in the presence of a spectral photosensitizer, are subjected to the imaging effect of imaging energy, and of development, advantageously of developing energy, causing a change in the tellurium-organic imaging material in the imaged areas accompanied by a change in the detectable characteristic of the imaging material in the imaged areas. The aforesaid imaging material is especially advantageously extended in a matrix of a polymeric or resinous film-forming material. The invention in its generally most advantageous form involves an imaging step employing imaging energy and producing a latent image, followed by a heat development step to produce the detectable recorded information or image.

28 Claims, 5 Drawing Figures

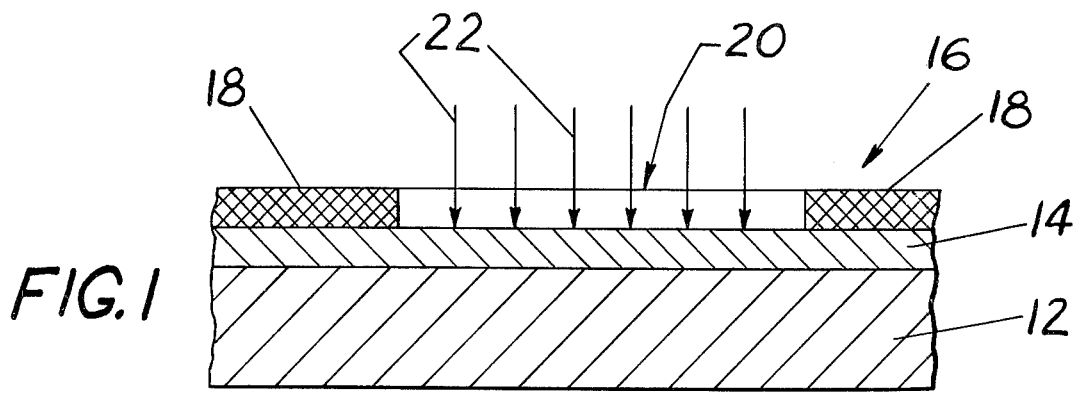
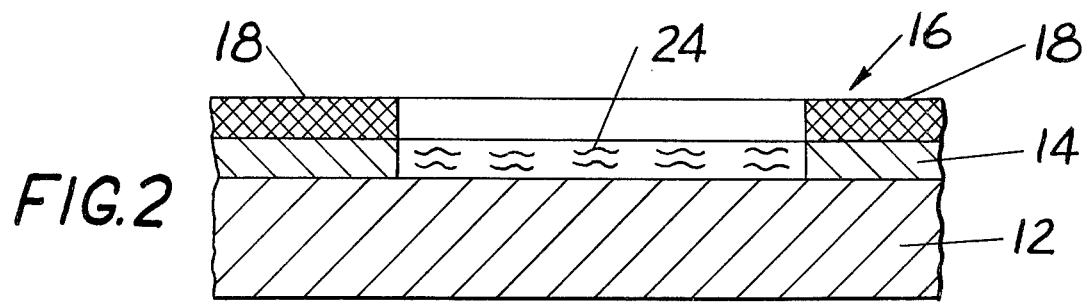
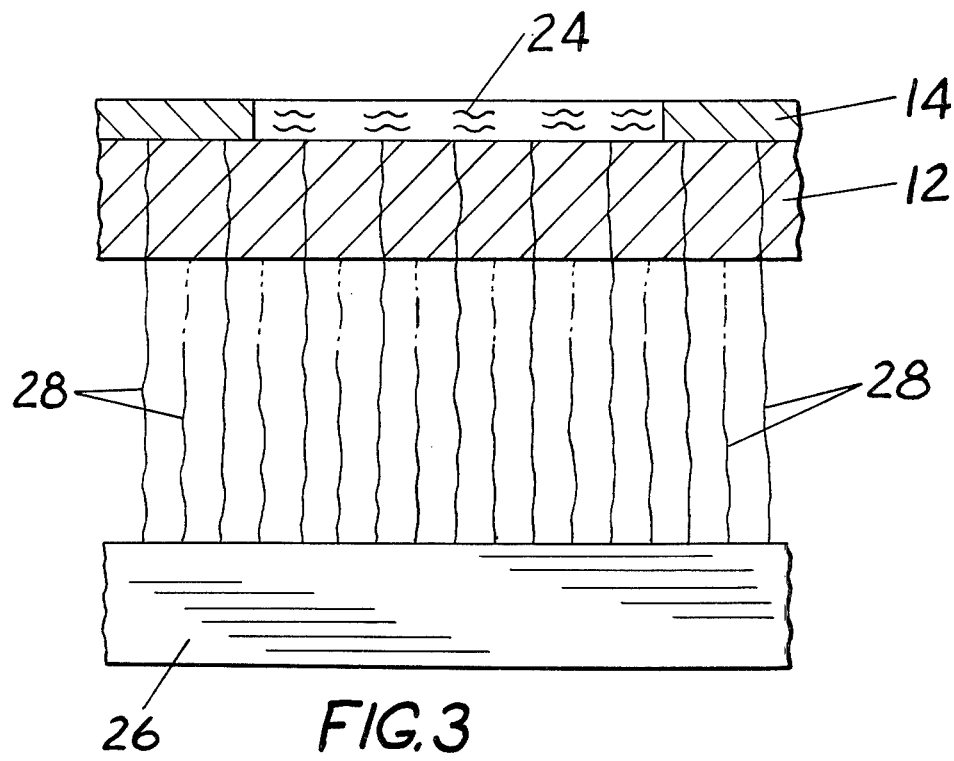

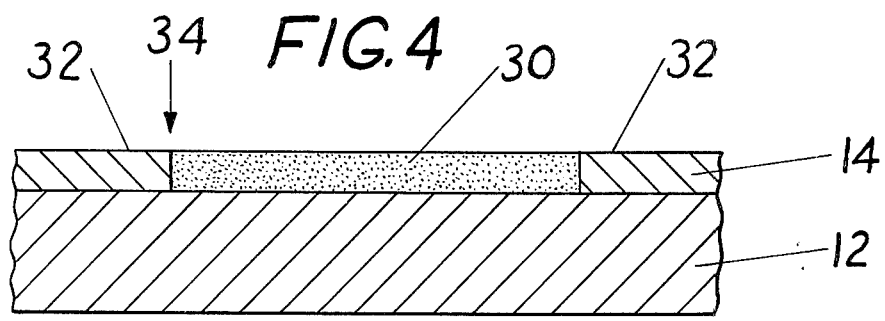
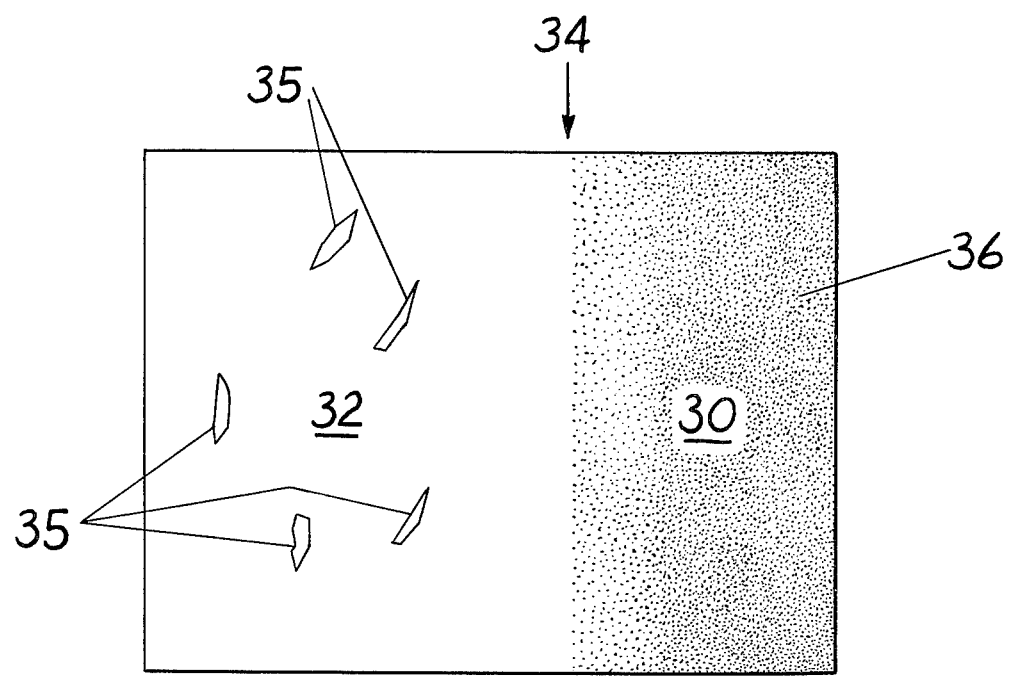

IMAGING AND RECORDING OF INFORMATION UTILIZING A TELLURIUM TETRAHALIDE COMPLEX OF AN AROMATIC AMINE

CROSS-REFERENCE TO RELATED APPLICATION

This application is a continuation-in-part of application Ser. No. 596,617, filed July 17, 1975, now abandoned, which is, in turn, a continuation-in-part of application Ser. No. 384,089, filed July 30, 1973, now abandoned.

Various methods are known for producing images or duplicates of images. The imaging materials used are, in certain cases, particular inorganic compounds and, in other cases, particular organic compounds. Some of these heretofore known methods employ mixtures of inorganic compounds such as silver halide, or silver salts or copper salts or other metal salts, with various types of organic compounds as sensitizers, in admixture in a film-forming carrier.

The present invention is concerned with a new imaging system which employs, as the imaging material, image-forming tellurium tetrahalide adducts of aromatic amines in which nitrogen attached directly or indirectly to the aromatic radical is substituted by alkyls each containing from 1 to 4 carbon atoms, the halide of said tellurium tetrahalide being chlorine, bromine, iodine or fluorine, particularly chlorine, said image-forming adducts being of one structure having one detectable characteristic and which is capable of undergoing a change, such as a chemical change, in response to the application of energy to produce a material of different structure having another detectable characteristic. Numerous embodiments of said image-forming adducts are disclosed hereafter. The aforesaid image-forming adducts used in accordance with the present invention are not diazonium compounds and are free from any diazo groups. Diazonium compounds or organo compounds containing diazo groups have long been known to be photodecomposable and as being very sensitive to light and have been utilized widely in imaging processes, illustrative of such prior disclosures being the Boudreaux et al articles in J. Amer. Chem. Soc., Vol. 80, (1957), pp. 1588–1590 and Vol. 85, (1963), pp. 2039–2943.

In the particularly important embodiments of the invention, the aforesaid image-forming or imaging adducts are incorporated into a matrix together with a spectral photosensitizer (hereafter, for convenience, called "sensitizer",) all as is hereafter described in detail. The resulting combination of materials is formed into a thin film or layer which is capable of producing a latent image when subjected to imaging energy as, for instance, actinic radiation or electromagnetic radiation. The resulting latent image may then readily be developed into an image of excellent contrast by wet development procedures, or by dry development procedures as, for instance, by subjection to a source of developing energy, generally in the form of or including heat energy.

Accordingly, the invention provides novel teachings and novel articles or compositions for producing records of retrievable information, for instance, images and duplicates of existing images, which are predicated on a layer which comprises image-forming or imaging adducts as described above which are of one structure and have one detectable characteristic and which are capable of undergoing a change in response to the application of imaging energy to produce a material of different structure, having another detectable characteristic, and which difference in detectable characteristics may be detected by any suitable detection means or read out means. The material having a different structure and different detectable characteristics, resulting from the imaging step, will sometimes hereinafter be called the image former.

As will be discussed in further detail below, it has been found that the imaging adducts here involved possess certain properties which adapt them especially for use in imaging processes. Notable is the fact that, as a result of the imaging and development steps, described hereafter, metallic tellurium is deposited from said adducts. While tellurium is not actually a metal, it does have some metallic characteristics and acts as a metal in some respects, and in some instances the deposited tellurium is referred to herein as metallic tellurium. Tellurium is chain forming in character and it is generally deposited from the adducts in chain form, which preferably includes thin needles, which are capable of rapid nucleation and growth of crystallites, which crystallites grow as chains and largely or mainly as needles. Such chains or needles are opaque and are characterized by excellent light-scattering properties, and they produce optical densities which are observed after thermal or other development; and such effects as may involve oxide formation are substantially restricted to surface effects as distinguished from causing degradation through the bodies of said chains or needles.

The following are illustrative examples of the foregoing imaging adducts or imaging materials (1) $((CH_3)_2N\ C_6H_5)_2TeCl_4$
(2) $((C_2H_5)_2N\ C_6H_5)_2TeCl_4$
(3) $((C_3H_7)_2N\ C_6H_5)_2TeCl_4$ (4) 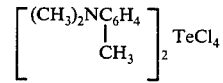

(5) 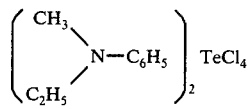

(6) $(C_6H_5N_2C_6H_4N(CH_3)_2)_2TeCl_4$
(7) $(C_6H_5N_2C_6H_4(C_2H_5)_2)_2TeCl_4$ (8) 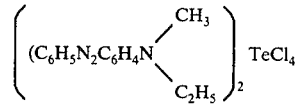

(9) $((CH_3)_2N\ C_6H_5)_2TeCl_2Br_2$
(10) $((CH_3)_2N\ C_6H_5)_2TeBr_4$
(11) $C_6H_5N_2C_6H_4N\ (CH_3)_2)_2TeCl_2Br_2$
(12) $(C_6H_5CH_2N(CH_3)_2)_2TeCl_4$

(13) 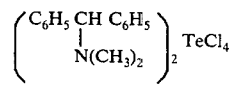

(14) $((CH_3)_2NC_6H_5)_2TeI_4$
(15) $((C_2H_5)_2NC_6H_5)_2TeF_4$

While, as shown above, the foregoing and other imaging compounds, the utilization of which falls within the scope of the present invention, can be used in the form, for instance, of their corresponding bromides and iodides, said imaging compounds in the form of their chlorides are distinctly preferred in at least most cases.

Various of the foregoing compounds are per se known compounds, as shown, for instance, by G. T. Morgan et al, J. Chem. Soc., (1929), pp. 1103–1111, although their utility for the purposes of the present invention has not heretofore been known or suggested. Thus, while the aforesaid Morgan et al article discloses the compound bisdimethylaniline tellurium tetrachloride and also states that it has a bright yellow color which deepens on exposure to light, neither said article nor any other prior art of which we are aware discloses or suggests that the particular imaging materials utilized in accordance with out present invention are capable of forming latent images when subjected to imaging energy in the form of particle or wave radiation, after which such latent images can be converted, by development, such as by heat, to an image of a different structure which is, generally speaking, visible to the naked eye and is defined by crystals of metallic tellurium. Others of said compounds, so far as we are aware, have not heretofore been known or prepared.

Compounds exemplified by Example (1) can conveniently be prepared by reacting two equivalent moles of the amine with one equivalent mole of the $TeHal_4$ in a solvent such as chloroform whereupon a solid precipitates out. The procedures shown in the book "Tellurium" by W. C. Cooper, Van Nostrand Reinhold Co., 1971, or modifications of such procedures are applicable to the production of such compounds.

The imaging materials of the present invention can also be present in the form of organo-tellurium polymers. Thus, for instance, any of the foregoing imaging materials (1) to (15) or similar imaging materials can be condensed with polymer ketones, such as acetylpolystyrene, acetyl-methylpolystyrene and polyvinyl methyl ketone, illustrative of which is the following:

The compound of Example (1) ($8.5 \times 10^{-3}$ mole) and acetylpolystyrene ($4.0 \times 10^{-3}$ mole) in chloroform are stirred for two hours. Removal of the solvent gives a solid which is then washed with diethyl ether. This and similar polymers can have variable molecular weights, the polymers from which they are produced, such as acetylpolystyrene, commonly having molecular weights generally in the range of about 2,000 to about 30,000, but which may be somewhat lower or very substantially higher. The finished polymers can serve not only as imaging materials but dually as the matrix or in admixture with other imaging materials and/or other matrix materials for the achievement of the objectives and in accordance with the teachings of the present invention.

At least in many, if not in most, cases, if the imaging adducts or imaging compounds here involved are of a character such that, when heated to the melting temperature thereof and maintained at such temperature for a reasonable period of time, they decompose to produce metallic tellurium, then they will be useful as imaging material when employed under the conditions and for the purposes of the present invention. Such imaging compounds or adducts are, for the purposes of the present invention, hereafter generally characterized generically as "imaging organo-tellurium materials."

At least many of the imaging organo-tellurium materials described above, although, for convenience, designated herein as imaging organo-tellurium materials, require the utilization in conjunction therewith of a spectral sensitizer, which, as noted above, will hereafter, for convenience, be referred to simply as "sensitizer," in order to produce a latent image when subjected to imaging energy or actinic irradiation, such as ultraviolet light or visible light, or other forms of imaging energy. In certain cases, impurities present as a result of the commercial manufacture of the imaging organo-tellurium materials function as sensitizers. In certain other instances, some breakdown of an imaging material, for instance, through hydrolysis, produces two species of degradation products, one of which can function as a sensitizer and the other as a source of tellurium. In other cases, and, in generally predominately the number of cases, a separate sensitizer is required to be added in order to produce a latent image or a sufficient latent image upon exposure of the imaging material to imaging energy which thereafter, on development by exposure, for instance, to dry heat, or by wet development, or by a combination of wet development and heat, results in production of the final image.

The matrix materials, into which the imaging organo-tellurium materials, and the separate sensitizers when employed, are incorporated to produce the imaging film or coating, are solids at room temperature, and they can be selected from a relatively large number of materials. They should desirably be at least in part of amorphous character and it is especially desirable that they be glassy, polar amorphous materials having a glass transition temperature, which desirably should not exceed about 200° C and may be as low as about 50° C, and, better still, should be within the range of about 80°–120° C. They are generally polymeric materials. Illustrative thereof are cyanoethylated starches, celluloses and amyloses having a degree of substitution of cyanoethylation of $\geq 2$; polyvinyl-benzophenone; polyvinylidene chloride; polyethylene terephthalate ("MYLAR"); cellulose esters and ethers such as cellulose acetate, cellulose propionate, cellulose butyrate, methyl cellulose, ethyl cellulose, hydroxypropyl cellulose; polyvinylcarbazole; polyvinyl chloride; polyvinyl methyl ketone; polyvinyl alcohol; polyvinylpyrrolidone; polyvinyl methyl ether; polyacrylic and polymethacrylic alkyl esters such as polymethyl methacrylate and polyethyl methacrylate; copolymer of polyvinyl methyl ether and maleic anhydride; various grades of polyvinyl formal resins such as so-called 12/85, 6/95 E, 15/95 S, 15/95 E, B-79, B-98, and the like, sold under the trademark "FORMVAR" - (Monsanto Company). Of especial utility is polyvinyl formal 15/95 E which is a white, free flowing powder having a molecular weight in the range of 24,000 – 40,000 and a formal content expressed as % polyvinyl formal of approximately 82%, possessing high thermal stability, excellent mechanical durability, and resistance to such materials as aliphatic hydrocarbons, and mineral, animal vegetable oils. These polymeric materials or resins and their preparation are well known to the art. In addition to their functioning as carriers for and holding together in a unitary composition the imaging organo-tellurium materials, sensitizers and any other ingredients which may be incorporated into the imaging film or coating or layer and their functioning as dry or essentially dry film-forming materials to provide thin films and providing mechanical durability in the finished imaged film, at least many of them appear also to play a chemical or physical role in the imaging process by providing, importantly, a source of readily easily abstractable hydrogen and, thus, appear to play a significant role in the latent image formation mechanism, as discussed hereafter. However, as indicated, the present invention is not limited to the use of such latter types of matrix materials. In certain instances, it may be desirable to decrease the viscosity of the matrix, which can be done, by way of illustration, by the addition of certain plasticizers, for instance, dibutylphthalate or diphenylphthalate, which additions tend to result in the production of images desirably of higher optical densities but which, however, also tend to have the disadvantage of increasing background fogging.

It may be noted that matrix materials of the type which contain basic groups may complex with the imaging organo-tellurium materials and, therefore, to the extent that such complexing may occur, the use of such matrix materials should be avoided.

The sensitizers which are useful in the practice of the present invention can be selected from a large group. They should be soluble or homogeneously dispersible in the matrix material. Their selection for use in any particular imaging compositions is influenced, in part, by the spectral sensitivity ranges desired. Thus, for instance, in the case of ultraviolet (UV) and visible sensitizers, the following are illustrative of those which can be employed and their approximate spectral sensitivity range (nm):

| Sensitizer | Spectral Sensitivity Range (nm) |
| --- | --- |
| 9,10-phenanthrenequinone | 200 – 400 – 500 |
| | U.V. Visible |
| 1,1'-dibenzoylferrocene | 400 – 600 |
| 1-phenyl-1,2-propanedione | 400 – 500 |
| 2-hydroxy-1,4-naphthoquinone | 400 – 500 |
| Benzil | 400 – 450 |
| Furil | 400 – 480 |
| Diacetylferrocene | 400 – 450 |
| Acetylferrocene | 400 – 450 |
| 1,4-bis(phenyl glyoxal) benzene | 400 – 500 |
| O-Naphthoquinone | Up to about 560 |
| 4,5-Pyrinequinone | Up to about 530 |
| 4,5,9,10-Pyrinequinone | Up to about 550 |

In the practice of the present invention, 9,10-phenanthrenequinone is especially satisfactory.

The following are illustrative sensitizers which are sensitive in the range up to about 400 nm and, therefore, are useful only in the ultraviolet range: benzophenone; acetophenone; 1,5-diphenyl-1,3,5-pentanetrione; ninhydrin; 4,4'-dibromobenzophenone and 1,8-dichloroanthraquinone.

Various other sensitizers can be utilized, particularly those of the type of substituted or unsubstituted polynuclear quinones, of which class some have been mentioned above, and others of which are 1,2-benzanthraquinone; 2-methylanthraquinone; 1-chloroanthraquinone; 7,8,9,10-tetrahydronaphthacenequinone; 9,10-anthraquinone and 1,4-dimethylanthraquinone.

It will be understood that not all sensitizers will be effective or equally effective, with each given organo-tellurium imaging material, even taking into account the utilization of imaging energy in the nm sensitivity range of the sensitizer employed and that suitable selections of combinations of particular organo-tellurium imaging materials and particular sensitizers will be required to be made for achieving desirable or optimum results. Such selections, however, can be made relatively readily.

In general, in connection with the foregoing matters, it may be noted that sensitizers have $n,\pi^*$ states, both singlet and triplet, of lower energies than $\pi,\pi^*$ states and, at least in most cases, compounds which have their $\pi,\pi^*$ states of lowest energy will not be photosensitively effective, although, in certain limited cases, compounds which fulfill the test of having lower energy $n \rightarrow \pi^*$ than $\pi \rightarrow \pi^*$ transitions do not function as photosensitive reactants. However, the above consideration is, in the main, an effective one for determining in advance whether a given compound will function as a photosensitizer for use in the practice of the present invention. In any event, a simple preliminary empirical test in any given instance can readily be carried out if desired.

For imaging purposes where a transparency is to be produced or where the image is to be detected by reflection viewing, it is, at times, preferred that both the matrix of amorphous material and the imaging organo-tellurium material are transparent or at least translucent and have little or no color. On the other hand it may be desirable to provide some color in the layer of imaging organo-tellurium material so as to favor the absorption of energy of a certain wave length. Hence, the senitizers which are utilized can be selected to reflect the desiderata involved. Thus, they can be of a type which are colored, or of a type which decompose to form colorless and transparent or translucent decomposition products.

In the imaging compositions, the proportions of the matrix, the imaging organo-tellurium material and the sensitizer are variable. In those special cases where the imaging organo-tellurium material utilized is one which also inherently or concomitantly possesses desired sensitizing properties, as noted above, a separate sensitizer is not necessary. It may, however, even in such cases, be desirable to employ a separate or added sensitizer which may be of entirely different sensitizing properties from that inherently possessed by the particular imaging organo-tellurium material utilized. In any event, generally speaking, excluding the organic solvent or solvents, where employed as described below, at least in most cases the matrix material, which is a normally solid material, that is, solid at room temperature, will be employed in amounts in excess of any one of the other materials and will also usually be present in major amount, that is, more than 50% and broadly in the range up to 90%, preferably about 60 to 70%, by weight, of the total materials present in the imaging composition. The imaging organo-tellurium material, generally also a normally solid material, will usually or commonly be the next largest ingredient, and will ordinarily constitute from about 5 or 7 to about 30%, usually about 10 or 15 to 20%, by weight of the imaging composition. The sensitizer, where it is a separate ingredient, which is usually a solid but may be a liquid at room temperature, will usually be employed in lesser proportions, commonly of the order of about 5 to 20%, usually about 6 to 15%, by weight, of the imaging composition, although, in certain cases the proportions thereof can be substantially higher, approximately or even exceeding somewhat the proportions of the imaging organo-tellurium material. Again, and with further regard to the proportions of the aforesaid ingredients, it may be stated that the area density of the sensitizer, for instance, the 9,10- phenanthrenequinone, is desirably selected so that about 80% of the photons falling on the film in the region of the absorption bands of 9,10-phenanthrenequinone are absorbed. Considerably higher concentrations of 9,10-phenanthrenequinone would leave the dark side of the film unexposed and no advantage would thus be served. Again, in general and for optimal results in many cases, the mole concentration of the imaging organo-tellurium material should be reasonably close to or roughly approximate that of the sensitizer. The concentration of the polymer matrix material should be sufficient to produce an essentially amorphous film without bringing about precipitation of the imaging organo-tellurium material, the sensitizer and other supplemental ingredients when utilized. Excess polymer matrix material also tends to decrease the sensitivity of the film.

In certain cases, it may be desirable to include in the imaging composition, additional or supplemental materials for obtaining certain or special effects. Thus, for example, it has been found that certain materials enhance the shelf life of unexposed virgin dry film compositions of the present invention and, in certain instances, also, they enhance the sensitivity of said film compositions. Illustrative embodiments of such additional or supplemental materials, which contain ether or polyether linkages in the molecules thereof, are such materials or polymers as polyethylene-20 sorbitan monolaurate; polyethylene-20 sorbitan monooleate; Polyox-10; Polyox-80; Polyox-750; polyethylene glycol-400 distearate; polyethylene glycol-600 distearate; poly (1,3-dioxolane); poly (tetrahydrofuran); poly (1,3-dioxepane); poly (1,3-dioxane); polyacetaldehydes; polyoxymethylenes; fatty acid esters of polyoxymethylenes; poly (cyclohexane methylene oxide); poly (4-methyl-1,3-dioxane); polyoxetanes; polyphenylene oxides; poly [3,3-bis (halomethyl) oxocyclobutane]; poly (oxypropylene) glycol epoxy resins; and copolymers of propylene oxides and styrene oxides. Such materials can be incorporated in the imaging film compositions in varying amounts, generally from 5 to 20% by weight of the solid imaging film compositions. In certain cases they enhance or prolong the shelf life or storage life, under given storage conditions, as much as 50% or even very substantially more timewise, and, as indicated, they also, in various cases, effectively increase film sensitivity.

Again, the inclusion in the imaging films of reducing sugars has been found, generally speaking, to bring about an enhancement in density of the image area (O. D. image-O. D. background), when the film is imaged as disclosed above and then developed, for instance, at about 120°–150° C and for of the order of about 15 seconds, especially where the imaging film is freshly prepared or not older than about a day after initial preparation. Such films, when exposed to imaging energy and then developed resulted in the production of a positive image (i.e. the optical density is greater in the nonexposed areas than in the exposed areas) in contrast to the negative working system which exists in the usual practice of the present invention. The inclusion of reducing sugars in the imaging compositions also enables development of the image, after exposure to imaging energy, to take place at lower temperatures, even at room temperatures, in a period of several hours, for instance, commonly in 10, 12 or 15 hours. The reducing sugars which can be employed are many, illustrative of which are dextrose, glucose, arabinose, erythrose, fructose, galactose, fucose, mannose and ribose. Especially effective are dextrose, arabinose, galactose, fucose and ribose. The reducing sugars can be used in variable amounts, but generally in equivalent amounts, or somewhat smaller or greater, in relation to the amount of imaging organo-tellurium materials in the imaging compositions.

In the production of the films or thin layers of the imaging material compositions, which are generally prepared in the form of solutions or homogeneous dispersions and coated or laid down on a substrate, it is especially desirable to dissolve or homogeneously disperse the ingredients in an organic solvent. Illustrative of suitable solvents are dimethylformamide (DMF), chloroform, tetrahydrofuran (THF), dimethylacetamide (DMA) dioxane, dichloromethane and ethylene dichloride, or compatible mixtures of such organic solvents or with other organic solvents. After the solution or homogeneous dispersion is filmed on a substrate in any suitable manner, the major proportions of such organic solvent or solvents are evaporated off, preferably at a relatively low temperature and, sometimes desirably, under subatmospheric pressures or in vacuo, until the film or coating is substantially dry to the touch, such dry to the touch coating being especially desirable for handling and processing purposes. Although such films or coatings may be, generally speaking, dry to the touch, it should be understood that this does not mean that the film is free from organic solvent. Indeed, it has been found that it is frequently very desirable that the finished films or coatings, prior to exposure to imaging energy, contain a small percentage, commonly of the general order of about 2 to 3%, by weight of the film or coating, of organic solvent, for instance, dimethylformamide (DMF), since its presence appears to play a favorable role in the sensitivity of the system in relation to the latent image formation and/or ultimate image obtained after the development step. The elimination of all or essentially all of the DMF, or other organic solvent or solvents, from the virgin film prior to the imaging and development frequently leads to a decrease in sensitivity. In any event, in any given instance where drying of the virgin imaging film has been carried out to a point where essentially no organic solvent is present, and whereby sensitivity is unduly reduced, sensitivity can be increased or restored by adding a small amount of organic solvent to the film prior to exposing it to imaging energy.

The imaging film or coating thickness is variable but will usually fall within the range of about 1 to about 35μm with about 5 to 15μm generally being a good average. In thickness in terms of millimeters (mm), such may vary from about 0.0005 to about 0.05 mm, or much greater such as from 0.05 to 5 mm, the selected thickness being dependent upon the particular use to which the imaging film is to be put.

The production of the imaging organo-tellurium materials, and the coating, handling and processing operations, to the extent which may be required, are carried out under appropriate light conditions, as those skilled in the art will readily understand. For instance, the formulation of the coating compositions and the coating and drying operations are conveniently carried out under amberlite filtered light (weak transmission at 550 mm). The dry film, prior to imaging, is desirably stored in the dark. In certain cases, avoidance of contact of certain of the ingredients with certain metals may be in order where undesired reactions, such as reductions, may occur. In general, the vessels or containers, stirrers, etc. utilized should be made of glass or other vitreous materials or other materials inert to the coating ingredients to insure against contamination or possible undesired reactions. It is advantageous, in general, to prepare the imaging compositions shortly prior to coating them on the selected substrate. Under suitable storage conditions, which generally are conditions of darkness and reasonable avoidance of air or oxidizing atmospheres and humidity conditions, the stability of the imaging compositions is good. Adverse and unduly prolonged storage, however, adversely affects speed and contrast in the production of the images.

In the utilization of the imaging films or layers of the present invention, they are subjected, for instance, through a suitable or desired mask, to imaging energy which may, for instance, be by actinic light, irradiation with ultraviolet light or by visible light, depending, for example, upon the specific imaging organo-tellurium material and the specific sensitizer utilized, to form a latent image which is normally not visible to the naked eye. In an illustrative case, for instance, in Example D below, illuminating with a Xenon lamp, the total flux delivered to the film surface may be in the general range of $3 \times 10^5$ to $10^6$ ergs/cm$^2$ of film. The subsequent development, to develop or bring out the latent image, is most desirably effected by the application of heat, for example, at a temperature of about 130°–160° C, preferably about 150° C, for several seconds, say 3 to 15 or 20 seconds, or wet development, or a combination of heat and wet development. Heat or thermal development can be effected by various means such as a hot plate, hot mineral oil, or hot silicone oil, at the aforementioned temperatures, or an infrared lamp. The result is to produce a dark image having, for example, an optical density (O.D.) of 1, in the area of exposure only, the background remaining generally relatively light or clear.

In the development step, only s small percentage of the total imaging organo-tellurium material which is present in the matrix composition is reduced to metallic tellurium. After the development, the film or layer may be, and desirably is, subjected to a fixing step which serves to effect removal of the sensitizer and to inactivate the unreacted imaging organo-tellurium material. While this can be accomplished in various ways, a particularly effective procedure is to contact the film, by washing or wiping with, or spreading on, or dipping in, chloroform/toluene (20:80 by volume) solution saturated with ammonia or with organic amines. This removes the sensitizer and, of course, the color thereof, and inactivates the imaging organo-tellurium material so that no image will form with subsequent exposure and heating and, thus, stabilizes the film. Organic amines such as trimethylamine, triethylamine, diethylamine, triisopropylamine, aniline and benzylamine (e.g. 10% solutions), are illustrative of those which can be utilized. Particularly when fixed, the film does not darken, generally speaking, unless subjected to somewhat elevated temperatures as, for instance, of the order of about 90° to 100° C.

The following examples are illustrative of the production of films or layers made in accordance with the present invention. They are not to be construed in any way as limitative of the invention since many other films or layers can be made in light of the guiding principles and teachings contained herein.

EXAMPLE A 50 mg of the compound of Example (1) above, 250 mg polyvinyl formal ("FORMVAR" 15/95E), 20 mg O-Naphthoquinone and 3 ml DMF are stirred together at room temperature until a homogeneous viscous solution is obtained. It is then poured onto a 3" × 4" sheet of "MYLAR" to form a film or layer of a thickness of about 10μ, and then heated in an oven at 50° C for about 30-45 minutes, at which time the film or layer is dry-to-the-touch.

EXAMPLE B

Example A is carried out as described therein except that chloroform is used in place of DMF. The film is dried in a well ventilated hood for 30 minutes at room temperature to form a dry-to-the-touch film.

EXAMPLE C

Example A is carried out as described therein except that, in place of the DMF, a mixture of DMF and chloroform is used in volume ratio of 20% DMF - 80% chloroform. A dry-to-the-touch film is obtained.

EXAMPLE D 50 mg of the compound of Example (6) above, 250 mg polyvinyl formal ("FORMVAR" 15/95 E), 50 mg 9,10-Phenanthrenequinone and 3 ml DMF are stirred together at room temperature until a homogeneous viscous solution is obtained. It is then poured onto a sheet of "MYLAR" and dried, as described in Example A, to form a dry-to-the-touch film.

EXAMPLE E 50 mg of the compound of Example (12) above, 250 mg polyvinyl formal ("FORMVAR" 15/95 E), 20 mg 4,5-Pyrinequinone and 3 ml DMF are admixed and coated onto "MYLAR" and heated to form a dry-to-the-touch film, in the manner described in Example A.

EXAMPLE F 40 mg of the compound of Example (13) above, 200 mg cyanoethylated starch, 16 mg 4,5,9,10-Pyrinequinone and 2.8 ml DMF are stirred together at room temperature until a homogeneous viscous solution is obtained. It is then poured onto a 3" × 4" sheet of "MYLAR" to form a film or layer of a thickness of about 10μ, and then heated in an oven at 50° C for about 30-45 minutes, at which time the film or layer is dry-to-the-touch.

EXAMPLE G 2 g of the compound of Example (6) above are mixed with 5 g of cyanoethylated starch and dissolved in about 100 parts by weight of acetone. The solution is deposited on a glass plate to form, after drying, a film of about 10 micron thickness.

EXAMPLE H 25 mg of the compound of Example (1), 125 mg polyvinyl formal ("FORMVAR" 15/95 E), 50 mg polyoxyethylene (20) sorbitan monolaurate, 7 mg 9,10-phenanthrenequinone and 3 ml of a solution of DMF and chloroform, as described in Example C, are stirred together at room temperature until a homogeneous solution is obtained, which is then coated on a Mylar substrate and heated as described in Example A.

EXAMPLE I

An imaging composition is made using 0.050 g of the compound of Example (1), 0.020 g of 9,10-phenanthrenequinone, 0.25 g polyvinyl formal ("FORMVAR" 15/95 E) and DMF/dichloromethane-2.25/0.75 ml. The composition is coated uniformly onto a sheet of "MYLAR" having an area of 12 square inches and dried at 50° C for 45 minutes. It is then imaged by exposure to a xenon flash from a type 700 Honeywell flash gun for about 2m sec. It is then exposed by subjecting it to a heat lamp at 150° C for 20 seconds to produce a visible image with good contrast.

The invention will be further illustrated in connection with the accompanying drawings in which:

FIG. 1 is a schematical fragmentary cross-sectional representation of a starting structure of the invention comprising a layer containing an imaging organo-tellurium material and being selectively subjected to imaging energy through an opening in a mask.

FIG. 2 is similar to FIG. 1, indicating the latent image, though not visible to the naked eye, formed by the selective application of imaging energy.

FIG. 3 is similar to FIG. 2 but showing the mask removed and development energy being applied to the structure.

FIG. 4 is similar to FIG. 1 but showing the structure fully developed.

FIG. 5 is a schematic representation of a photomicrograph showing in a 2000X enlargement a portion of an area containing a deposit of crystalline image former.

Referring to the drawings, the structure shown in FIG. 1 comprises a substrate 12 such as glass, on which is deposited a thin, light transmissive layer 14 comprising a matrix of a glassy, amorphous material such as polyvinyl formal and distributed therein an imaging organo-tellurium material and a sensitizer, as shown, for instance, in illustrative Examples A-I, inclusive. Upon the layer 14 of the structure is placed an imaging mask 16 comprising opaque areas 18 and light transmissive area 20. Electromagnetic radiation or actinic light 22 is shown falling through light transmissive area 20 of the mask onto the portion of layer 14 underlying area 20 of the mask. The radiation is being applied in form of a short pulse. In FIG. 2 is shown the structure of FIG. 1 after termination of the application of electromagnetic radiation. In layer 14 is indicated by small wavy lines the presence of latent image 24, even though, as pointed out above, this latent image is generally not visible to the naked eye.

In FIG. 3 is shown the structure of FIG. 2, with latent image 24 in the center section of layer 14. The mask 16 has been removed. The structure is shown suspended above the source 26 of radiant heat energy, such as an electrical heater, the temperature of which is controlled in the desired range, for instance, 130°–150° C. Radiant heat energy 28 is shown to pass through substrate 12 to heat up the layer 14. As layer 14 is being heated a chemical reaction takes place in the area containing the latent image 24, whereby the tellurium of the abovementioned imaging material is set free from its bonding in the compound (1) and precipitated in elementary form in layer 14. The tellurium is present in the area corresponding to the latent image 24 in the layer 14 in form of needles or needle crystallites of very small size. The structure as it appears after completion of the heating step is shown in FIG. 4 comprising an opaque section 30 in the center, where the radiation strikes layer 14, and light transmissive section 32 representing the areas protected by the opaque areas 18 of mask 16 (FIG. 1) from the radiation.

If the substrate 12 is light transmissive or transparent, such as glass, upon viewing through the structure, area 30 is dark or essentially non-transmissive for light, while areas 32 are highly light transmissive. Such structure, therefore, represents a transparency.

If the substrate 12 is a non-transparent but highly reflective material such as white paper and layer 14 is originally light transmissive, upon viewing, area 32 will appear white and show the reflectance of the paper, while area 30 is non-reflective appearing dark or black upon reflective viewing.

The separation line at 34 in the structure of FIG. 4 is photographed at an enlargement of 2000X. The appearance of the photomicrograph so obtained is schematically represented in FIG. 5. The separation line of transparent and opaque areas is indicated by the arrow at 34. To the left in the light transmissive area 32 appear no or only a few larger crystals 35 of tellurium while to the right clouds of small particles 36 can be seen. By visual inspection under the microscope it is seen that there are scattered particles of tellurium needles in the layer 14 which produce the opaqueness of area 30.

In the example of the image illustrated in FIG. 5, the tellurium particles representing the image former in area 30, preferably and advantageously in the form of needles, have a very narrow size distribution. This is a very favorable characteristic of the imaging organo-tellurium materials of the present invention, since it permits the making of high quality images of uniform properties. It permits also to produce a well-balanced gray scale. By varying the composition of the imaging organo-tellurium materials, by varying the concentration of the imaging organo-tellurium materials in the glassy matrix material and/or by varying the proportion of the sensitizer and by adjusting the imaging and developing conditions, such as the intensity and duration of application of the imaging energy and the intensity and duration of the application of the developing energy, the tellurium particle sizes, notably the length of the tellurium needles constituting the image former, may be controlled. Depending on the intended use of the image, one will favor extremely small size needles. In certain cases, increasing the length of the tellurium needles will increase the relative density and contrast, but may reduce the resolution potential of the system. In general, the greater the length of the tellurium needles, leaving everything else equal, the more pronounced will be the photographic gain and the photographic speed of the system. The selection of particular imaging organo-tellurium materials which possess variable chemical or other reactivity enables the production of novel photographic systems which, with respect to the resolution, sensitivity to ambient light, photographic sensitivity, speed of development and access to the image, fill various of the needs for which photographic systems are presently used or may be beneficially used.

In another illustrative embodiment of the present invention, utilizing the imaging film of Example F in the structure shown in FIG. 1, an electronic flash gun is used to provide an about 1 millisecond flash of broad spectrum light. The layered structure is then placed for 3 to 15 seconds onto a hotplate, at a temperature of about 130°–140° C, whereby almost instantly a sharp image appears which is an exact negative duplicate of the image represented by the imaging mask. The image has excellent resolution and sharpness.

Although the imaging organo-tellurium materials used in the preparation of the imaging film are commonly crystalline in character, the virgin film as laid down in a dry-to-the-touch film on the substrate, and prior to the initial imaging step, appears generally or usually to be non-crystalline so far as has been determined by X-ray diffraction testing. After the development step, the metallic tellurium, advantageously in needle form, appears although particle size and shape due to nucleation and perhaps other forces cause modifications, the exact nature and character of which have not yet been fully delineated. The size of the metallic tellurium needles appears to be affected by such considerations as the imaging film thickness, the character and viscosity of the matrix, the presence and the amount of organic solvent in the film when subjected to imaging energy, and the temperature at which development is effected which also bears upon the color of the final image.

Depending on the desired result in the particular system used, the thickness of the layer 14 (FIG. 1) in the structure of the invention may be varied in wide limits, as heretofore noted. The layer containing the imaging organo-tellurium material may be as thin as 1000 Å or less and as thick as 1mm or more. For producing transparencies or reflection copies, layer thicknesses of about $0.2\mu m$ to about $20\mu m$ are generally moxt favorable. The most desirable thickness of the layer depends on such factors as the concentration of the imaging organo-tellurium material in the matrix, the nature of the image former, the maximum density desired, the differential in reflection or transmissiveness desired, and on many other factors. In each system one can readily determine the most favorable thickness of the layer by considering these factors. For certain purposes, such as recording information in data processing equipment, the layers of the imaging material may be much thicker or thinner than the above stated figures. The formation of nuclei and of the preferred image forming crystallites is influenced to some degree by the thickness of the film. Apparently, surface effects and interfacial effects must be considered in the nucleation reaction and in the reaction leading to the small image forming-crystallites. In selecting the most favorable film thickness of the imaging layer, therefore, also these factors must be considered.

Similar considerations apply to the selection of the concentration of the imaging material in the matrix material. Generally, it is desirable to use the imaging material in as high a concentration as is possible. The functions served by the matrix material have been noted above and require no reiteration. The matrix material itself, and the inclusion of plasticizers, if desired, tend to function as solvents for the imaging materials and to render the film, as deposited and dried, amorphous in character. The compatibility of the matrix material and the imaging organo-tellurium materials appears to add to the sensitivity of a given system and provides better images or better contrast and higher density.

Another relevant consideration is the relationship of the glass transition temperature of the matrix material and the temperature at which cleavage of the molecule of the imaging organo-tellurium material used in each instance occurs under the particular reaction condition and in the particular surroundings. If, for instance, the molecule of the imaging organo-tellurium material starts to decompose or cleave at a temperature much lower than that of the film, secondary reactions may take place locally which inactivate all or part of the cleavage products of the imaging organo-tellurium material which, therefore, lowers the efficiency of the particular imaging system. In certain systems it may be desirable that the cleavage of the imaging organo-tellurium material is initiated at a lower temperature than the glass transition temperature of the matrix material, and, when the glass transition temperature is reached in the development step, reaction products migrate to the nucleation sites, delivering the atoms of the metallic tellurium for the building up of the image-forming tellurium needles. Hence, by careful correlation of these factors, better imaging performance can be achieved.

With regard to the substrates, which have been mentioned above and of which certain illustrative examples have been given, it may be observed that the substrate may be any material capable of forming a film or plate, provided that it has a melting or softening point higher than the temperature utilized for the development of the latent image, and provided it is sufficiently unreactive so as not to interfere with the imaging reaction. Suitable substrates are glass, mica, polyamides, polyesters, polystyrenes, hardened condensation polymers such as of the epoxy type, etc. Many heat resistant polymers are commercially available which fulfill these conditions in an excellent manner, and which, therefore, are excellently suited as substrates in the imaging structure of the present invention. For most commercial applications of the imaging organo-tellurium materials it is desirable that the substrate be flexible so as to permit use in the form of continuous rolls in printers and in readers. If transparencies are to be produced in a particular imaging system, it is, of course, desirable that the substrate be light transmissive. On the other hand, if copies are to produced which are to be detected by reflection viewing, it is preferred that a substrate be used which has a high reflectance such as heavily filled white or colored cardboard and other similar structures.

In certain cases, if desired, the substrate may be omitted and layer 14 may be used as a self-supporting structure which is imaged and developed while, for instance, supported on a temporary supporting structure. In this case, the finished image structure consists merely of a thin film of the amorphous glassy matrix material containing incorporated therein the imaging organo-tellurium material and sensitizer, plus such additives or supplemental materials as may be used, and the image former precipitated therefrom and transformed therein.

While, as described above, the component ingredients of the imaging composition, namely, the matrix material, the imaging organo-tellurium material and the sensitizer, plus such additional or supplemental materials as may be incorporated therewith to obtain particular special properties, are admixed and embodied in a single layer, or as a single layer on a selected substrate, it is within the scope of the invention to utilize a multilayer system, more particularly a two-layer system. Thus, by way of illustration, one layer can include the sensitizer, for instance, 9,10-phenanthrenequinone carried or distributed in the matrix, for instance, a polyvinyl formal, and supported on a substrate, say a "MYLAR" sheet; and the other layer can include the imaging organo-tellurium material carried or distributed in the matrix, which may be the same or a different matrix but, desirably, is the same matrix, and said layer is, likewise, supported on a substrate, say, again a "MYLAR" sheet. Such additional or supplemental materials as may be utilized can be incorporated in whole or in part in either of said layers or distributed through both of said layers. Exposure to imaging energy is then carried out of only the layer containing the sensitizer in which the latent image is formed. The production of the developed or visible image can then be effected, for instance, by pressing the latent image layer against or onto the imaging organo-tellurium material containing layer, in generally sandwich form, and then subjecting the assembly to heat, say at about 150° C for, for instance, of the order of about 15 seconds, the heat being applied from either or both sides through the "MYLAR" substrate or substrates. An image of generally neutral tone promptly appears. This type of procedure provides a favorable alinement supply and with no criticality requirements.

In certain cases, preheating of the virgin imaging film, prior to exposure to imaging energy, at a temperature in the range of 80°–150° C for a few or several seconds, enhances resistance of the virgin imaging film to moisture without adversely affecting the sensitivity of the film.

As noted previously, various forms of energy may be used as the imaging energy and as the development energy. This may include particle energy and wave energy, such as, for instance electromagnetic radiation, heat electrons, electrical current, visible light, actinic light or radiation, monochromatic light, laser beams, X-rays, etc., particularly particle or wave radiation. The preferred energy depends also on whether a negative working or a positive working system is employed. In the imaging step, actinic light or electromagnetic radiation is generally used for this step, for instance, light of a wave length of 450nm using a Bausch and Lomb monochromator and a 150 watt Xenon lamp. In the case of the use, for imaging to produce the latent image, of an electron beam, the energy values are variable, generally falling into the range of about 2 Kev to about 100 Kev (a conventional television tube uses an electron beam of about 19 Kev). Thus, by way of illustration, using 50 Kev, in which case $E \lesssim 3 \times 10^4 e/cm^2$, a latent image is obtained which is then developed, for instance, to produce, in any of the manners disclosed herein, a visible image. Radiant electromagnetic radiation is usually best suited to produce an image by projection or by the use of a mask and the like. It is also generally suited best for producing an image having a desired gray scale or tonal gradation. Which kind of electromagnetic radiation or other radiant energy and which wavelength is used in a particular instance depends on the task to be performed and on the particular sensitivity of the imaging organo-tellurium material employed. Various of such imaging materials, in the presence of a sensitizer, inherently present or separately added, are sensitive to actinic radiation including laser energy and the like. If a given, selected imaging organo-tellurium material is per se insensitive to, or does not have its optimum sensitivity at, a wavelength of actinic light or electromagnetic radiation, which is to be used or available for imaging, selected sensitizers, as noted and indicated above, are added to render the said imaging material sensitive or to shift the sensitivity into the desired range. In this manner, one can, for instance, use an imaging organo-tellurium material which has its maximum sensitivity in the U.V. range of wavelength to a sensitivity in the range of visible light or for X-rays, etc. Similar considerations apply with respect to the energy used in the development step. Most desirably and advantageously, heat is used for the development. This may be radiant heat such as infrared radiation or microwaves or hot air or heat by contact and convection from a heated body, or it may be heat from a heated wet developing bath. The use of heat for the development offers the advantage that heat may readily be controlled as to intensity and duration. Heat is also inexpensively available from inexpensive equipment. However, if desired, any of the other energy forms may be used for bringing about development of the exposed imaging organo-tellurium material, provided it is susceptible to this form of energy.

In each of the imaging and development steps, a combination of different forms of energy may be used. In this case it is preferred to employ a combination of the energy most effective for imaging and of the energy most effective for the development. The development heat may also be supplied by heat generated by the absorption of electromagnetic radiation as is the case with lasers. Incandescent lamps, infrared lamps, laser beams, electronic or bulb photoflash units, mercury quartz lamps, etc. can be used for the imaging. In some cases, similar, as well as, of course, other sources can be used for the development.

The energy may be applied for different lengths of time depending on the intensity of the energy source used. With high energy imaging sources, pulses of a microsecond or less to a few milliseconds or more are commonly sufficient to complete the imaging. With lower intensity energy sources, longer times as, for instance, a fraction of a second to several seconds or from 20 to 90 seconds, or more, can be used. Depending on the intended use of the images and on whether or not insensitivity to ambient light is desired, one will select one or the other imaging organo-tellurium materials and adapt the imaging time and the intensity and the kind of imaging energy to the requirements of the selected imaging organo-tellurium material.

The time of development depends also to a degree on the intensity of the development energy employed, though in this case usually a threshold energy exists which must be exceeded. This threshold is one of intensity — of temperature in the case of heat energy — and must be exceeded to effect development. With the observance of this precaution, development is completed in a second or a few seconds or longer, for instance, of the order of 15 to 20 seconds or, generally, in the range of 5 seconds to 2 minutes, depending on the temperature utilized and on the nature of or the particular imaging organo-tellurium material used. The thickness of the layer of said imaging material and the thickness of the substrate may also affect the time required for development. However, in all instances, development is quite rapid so that the said imaging materials and the method of the invention provide reasonably rapid access to the finished stable image. Generally speaking, speed and contrast increase with higher temperatures and longer development times.

Depending on the composition of the imaging organo-tellurium material, for instance, it may be desirable to effect the development at a predetermined temperature. As stated, the temperature of development should be adjusted to a level above the threshold, at which the reactions, leading to the formation of the image former, to wit, the precipitation of the metallic tellurium needles, take place. On the other hand, the temperature should not be high enough to cause the thermally induced nucleation and reaction in the areas which have not been subjected to the imaging energy. Usually, the range between these two temperature limits is rather wide, and the temperature can be readily adjusted to fall into the intermediate, useful range. If these precautions are observed, an image of high contrast with low nucleation in the background areas is obtained. In general, where heat development, and particularly dry heat development, is employed, the development temperatures will commonly fall within the range of about 120°–170° C, it being understood that, generally, the lower the development temperature the longer will the heating time be required for producing the same optical density. Generally, also, there are, commonly, differences in shades of the final image depending upon the development temperature employed. Again, generally speaking, the effect of appreciably increasing the concentration of the imaging organo-tellurium material and the sensitizer is to enable lower development temperatures to be employed where thermal development procedures are utilized. In the thermal development step, depending upon the particular imaging organo-tellurium material employed but, for instance, in the case of such illustrative compounds as those of the above Examples 1, 2 and 3, volatiles are released, such as hydrochloric acid, during the initial stages of decomposition of the imaging organo-tellurium materials, which may, and appear to, have an accelerating or autocatalytic effect in the reduction reaction which ultimately results in the formation of tellurium needles and may play a role in such amplification as occurs in the development step.

Wet development can be utilized with or without heat, and, where heat is utilized in conjunction with wet development, such heat can be applied extraneously by a heat lamp such as an infrared lamp or the like, or the wet developing bath may be applied hot. Such wet development baths may be of various compositions, illustrative thereof being baths consisting of hot inert liquids such as vegetable oils or hydrogenated vegetable oils, silicone oils, glycerin, and the like, or such oils in admixture with minor proportions of DMF and/or a reducing agent such as hydroquinone or reducing sugars such as glucose and dextrose. The inclusion of various additives to the illustrative inert liquids may serve to substantially increase the effective photographic speed of the film, i.e., an appreciably higher optical density can be developed from a smaller exposure. A preferred combination of additives, liquids and bath temperatures is as follows: after exposure to imaging energy as, for instance, to actinic radiation, the film is first submersed for about 5 seconds into a bath consisting of 15 cc of toluene and 15 cc of silicone oil at a bath temperature of about 120° C. Thereafter, the film is placed into a second bath consisting of 20 cc of a vegetable oil (e.g. "CRISCO"), 10 cc dimethylformamide (DMF) and 90 mg hydroquinone, at a bath temperature of about 140°–150° C. The initial brief period (about 5 seconds) at about 120° C in the first bath serves to form small tellurium nuclei from the photolytically produced tellurium. In the second bath, the DMF swells the film, thereby facilitating rapid growth of the nuclei formed in the first bath with the tellurium generated thermally by the heat and chemically by the hydroquinone by reduction of the imaging organo-tellurium material. At the same time, the sensitizer, which desirably is 9,10-phenanthrenequinone, is leached out of the film, thereby rendering the image permanently fixed. The development time in the second bath may, for instance, be of the order of 60 to 90 seconds. The bath temperature, the DMF concentration and the development time are interchangeable parameters such that a lower bath temperature can be readily accommodated by adjusting the concentration of the DMF and the hydroquinone. The increase in photographic speed obtained with the above illustrative development procedure is of the order of 200 fold. This means that, whereas by means of dry development, simply heat as previously described, an optical density of 1.0 is obtained in the film with an exposure of about $10^6$ erg/cm$^2$, the bath development results in an optical density of 1.0 for an exposure of about $6 \times 10^3$ erg/cm$^2$ without adversely affecting the background density.

In any event, after initial exposure to imaging energy, the thus exposed or latent imaged film can be developed immediately or, if desired, even after days or many weeks in storage in the dark or under other non-development storage conditions.

In certain cases, after the formation of the latent image by exposure to imaging energy, the layer or film, prior to development, may be treated with an organic solvent or mixture of organic solvents, for instance, such as DMF or mixtures of DMF and acetone, to wash out the unreacted sensitizer, while leaving the latent image essentially unaffected. The said layer or film containing the latent image is then subjected to development energy to form the visible image. This procedure, in certain cases, appears to play a favorable role in regard to gain considerations.

The mechanisms of the reactions occurring in the practice of the present invention have not been entirely elucidated, but it appears that exposure of the compositions containing the imaging organo-tellurium materials to imaging energy causes the organo-tellurium materials to undergo an electronic alteration to an excited state brought about by energy transfer from the sensitizer and/or by direct excitation of the organo-tellurium molecule, with the formation of appreciable numbers of nucleation sites or points in the imaged areas and with substantially no or very few such sites or points in the unimaged areas. It appears, further, that absorption of the imaging energy by the sensitizer to form the nucleation sites or points occurs initially on exposure of the imaging organo-tellurium material and sensitizer (whether the latter is inherently present by reason of the particular chemical structure of the imaging organo-tellurium material, or by the presence of a decomposition product having sensitive properties, or by the addition of a separate or extraneous sensitizer) by a hydrogen abstraction mechanism from the polymeric matrix material or the like. The latent image is apparently the result of a chemical modification or photochemical reduction of the sensitizer by the imaging energy in the presence of the imaging organo-tellurium material. It appears, although not yet fully ascertained, that the initial latent image of nucleation sites or points which is formed is not defined, produced or delineated by metallic tellurium. It is possible that the initial latent image is made up of several, perhaps four or more, compounds, for instance, when 9,10-phenanthrenequinone or analogous compounds are used as the sensitizer. In any event, in the subsequent development step, which provides the needed energy to allow release of tellurium atoms from the organo-tellurium material at the nucleation sites or points, which is especially desirably effected thermally or by heat, the imaging organo-tellurium material, possibly in a metastable or unstable state, is converted by reaction mechanisms not fully understood but which may involve a reduction reaction by the hydrogen which was abstracted by the sensitizer from the matrix material or by the sensitizer carrying said abstracted hydrogen, whereby to produce a relatively appreciable number of very small metallic tellurium particles, mainly or substantially entirely and advantageously in the form of needles, on the aforementioned nucleation sites or points. Electrons can also act as reducing agents and the materials themselves can also cause reducing.

These metallic tellurium particles, advantageously in the form of needles, act an nuclei upon which further growth of metallic tellurium takes place principally at the ends of said needles to produce longer needles which form and delineate the final developed image. The formation of the metallic tellurium needles by the reduction of the imaging organo-tellurium material in the system, and under the conditions existent therein under the initial application of imaging energy followed by development energy, apparently brings about further enhancement of the release of metallic tellurium from the imaging organo-tellurium material, which forms a bountiful source of tellurium, to effect, as noted above, further buildup of metallic tellurium on the initially formed metallic tellurium needles and principally at the ends thereof to increase the length thereof. The length-wise growth of the tellurium needles may be enhanced by field concentration at the sharp ends of the needles. The optical density of the final visual image appears to be the result of resonant scattering in addition to light absorption by the tellurium needles. Optical density after development increases initially linearly and then logarithmically with exposure time.

The occurrence of the tellurium particles, which are crystalline in character, is largely or substantially ubiquitous throughout the matrix after development, but only in the illuminated areas are the tellurium crystallites of such dimensions as to optimize the scattering of light which is responsible for the desired visual image. The formation of nuclei which occurs in the background or non-image areas is very substantially less than in the image areas, and they are very widely spaced, and this fact, coupled with the possibly somewhat different character of such background nuclei, results in a relatively light background so that good contrast between the image area and the background area is achieved. Furthermore, by careful handling of the imaging organo-tellurium materials from the beginning of their production to the imaging, and by effectively excluding carrier-forming energy of damaging intensity prior to exposure to the imaging energy and up to the time of development, the number of metallic tellurium particles in the non-image areas can still be further reduced.

The foregoing discussion with respect to the matter of needle formation in the tellurium crystallites may be somewhat elaborated upon by a consideration of the following facts in relation, illustratively, to a film such as is produced pursuant to Example D above. In the virgin film, that is, prior to exposure to imaging energy, under examination using Transmission Electron Microscopy (TEM), dark areas appear which indicate the presence of aggregates of the compound of Example (6). The same film, exposed for 100 seconds at 400 nm and developed at 150° C for 15 seconds to an optical density of 1, shows tellurium needles having a length generally in the range of 1000 to 2500 Å and a diameter of about 100 Å which are responsible for the visible image. On the other hand, the same virgin or starting film not subjected to imaging energy but subjected directly to heat at 150° C for 15 seconds shows the presence of metallic tellurium but the presence of very little or the essential absence of tellurium in the form of needles. Finally, the same virgin or starting film exposed to imaging energy as described above in this paragraph but for a period of 70 hours at 450 nm, but not developed, showed an abundance of tellurium needles.

Light or energy absorbed by the sensitizer is effective for the formation of the latent image, and the exposed area becomes depleted in its content of the sensitizer in its original form in the film prior to exposure. Although, as has been indicated above, the latent image which is formed upon exposure to imaging energy is apparently not formed or delineated by metallic tellurium, it is possible that some metallic or crystalline tellurium, in very small amounts, may be present in the film after exposure to imaging energy and prior to the development step.

Briefly and generally, the imaging layer including the matrix, the imaging organo-tellurium material and the sensitizer, as expressed above, is essentially an amorphous structure and it has one detectable characteristic, as for example, it being substantially light transmitting. When the imaging layer is subjected to imaging energy, nucleation sites or points are established in the imaged area of the imaging layer to provide a latent image therein. When the so imaged layer is subjected to development energy, such as heat, the imaging organo-tellurium material is reduced and deposits small crystalline metallic tellurium particles at said nucleation sites or points in the latent image, advantageously in the form of small needles, forming small crystalline metallic tellurium nuclei upon which further metallic tellurium is deposited by the further reduction of the imaging organo-tellurium material to provide larger crystalline metallic tellurium particles or needles in the imaged area. Thus, the initial structure of the imaging organo-tellurium material is changed to a different structure in the imaged area, a crystalline metallic tellurium structure, having another detectable characteristic, for example, it being substantially non-light transmitting. In effect, therefore, the essentially amorphous structure of the imaging layer which is substantially light transmitting is transformed in the imaged area to an essentially crystalline structure which is substantially non-light transmitting to form a visually detectable image. This is accomplished by the various materials, the relations and reactions between the materials and the transformation processes and mechanisms described herein.

In summary, therefore, the mechanisms which come into play in the present invention are presently postulated to involve the following considerations:

1. A photosensitive organo-tellurium material or adducts as defined above, which is capable of excitation, under the influence of imaging energy, and in the presence of a sensitizer, to a reactive state and optimumly with good efficiency.

2. The $n\pi^*$ singlet and/or the $n\pi^*$ triplet are the most reactive states, and preferably are the lowest states of the sensitizer.

3. The matrix advantageously conains readily easily abstractable or extractable hydrogen atoms.

4. The excited state possesses sufficient energy and a sufficient time period advantageously to permit abstracting hydrogen atoms from the matrix by the sensitizer.

5. The aforedescribed organo-tellurium material or adduct is one which is reactive toward a metastable intermediate to yield Te° needles.

Films made in accordance with this invention may have high photographic resolution, for instance, in various cases, of the order of 500 to 600 line pairs/mm and good continuous tone with gamma close to unity.

The shelf life of the latent image is, generally, good. On unduly prolonged storage, however, of the order of several days or more, development tends to occur at materially lower temperatures than would otherwise be necessary to obtain effective thermal development. Contact of the latent imaged films with various solvents, and dry, wet or low temperature storage generally does not adversely affect the quality of the final image obtained after subsequent thermal development of the latent image.

As to the developed image, its stability is, generally speaking, also good, except, for instance, in the presence of oxidizing agents which cause fading of the image.

The foregoing discussion of the present invention shows that it provides an excellent imaging system which may be widely used for a variety of imaging tasks. The materials of the invention may be employed in the camera, for proofing purposes and for duplication of images, for making duplicate copies of microrecords and microfiche, for recording output information of a computer and for the output of other data storage and retrieval systems. The broad usefulness of the new imaging system of the invention is predicated on the quick and ready access to permanent copy of the information of the record or image. Different methods of readout can be used based upon differences in reflectivity, transparency, opaqueness, electrical properties, the ability to hold electrical charges, etc. The records and images are sharp and have good to excellent resolution. The organo-tellurium imaging materials used in the practice of the present invention can be varied from a low gamma to high gamma as may be needed and desired in each individual instance.

In this respect, the new imaging system, generally speaking, has much of the versatility of the established silver halide system, which by choice of emulsions and development conditions also permits a wide variety of gammas. However, as is readily apparent from the foregoing, the imaging system, as well as the development system, proper, of the present invention does not require wet treatments and, moreover, it provides rapid access to the finished, stable image which is many times not the case with the silver halide images. This makes the new system, particularly in such instances, superior in numbers of respects to the established silver halide systems.

The various other imaging systems which are being used or have recently been proposed as not requiring a wet treatment usually have the disadvantage that they are predicated on the use of a single photosensitive material with little possibility of varying the character of the material such as varying the gamma of the image. They may, therefore, be suitable in one particular application but are not suitable in any other applications. The imaging organo-tellurium materials used in the imaging system of the present invention are, generally speaking, inexpensive and may readily be applied by inexpensive methods so that a low cost imaging system is provided.

The present invention does not require vacuum deposition or sputtering of an elementary image former onto a substrate. The imaging compositions may readily be applied in form of a solution e.g. by wiping, spin deposition, application by a doctor knife, etc. The images produced by the practice of the present invention can be used as a print master, e.g. when an image former is selected which has a capacity for accepting and holding electrical charges differently from the matrix material. In this case, the images can be produced, for instance, on a paper or cardboard substrate to provide an inexpensive, throwaway printing master. After a desired number of copies have been made from it, the print master is simply discarded.

We claim:

1. A method for producing a record of retrievable information comprising:
providing a layer including an imaging organo-tellurium material and a separate spectral sensitizer, said imaging material and said sensitizer being carried in a polymeric matrix material comprising said layer, said imaging material being in the form of a tellurium tetrahalide adduct of an aromatic amine in which nitrogen attached directly or indirectly to the aromatic radical is substituted by alkyls each containing from 1 to 4 carbon atoms and being free from diazo groups, said imaging organo-tellurium material being of one structure and having one detectable characteristic which is capable of undergoing a change in response to the application of imaging energy to produce a material of different structure having another detectable characteristic,
the step of applying imaging energy in the form of particle or wave radiation to certain portions of said layer to bring about in said certain portions of said layer the formation of a latent image, at which said imaging organo-tellurium material can be changed to said different structure having said other detectable characteristic.

2. The method of claim 1, in which said imaging energy comprises electromagnetic radiation.

3. The method of claim 1, in which said polymeric matrix material is at least in part of amorphous character and in which said imaging material is dissolved or dispersed.

4. The method of claim 1, in which the tellurium tetrahalide is $TeCl_4$.

5. The method of claim 1, in which said polymeric matrix material serves as a source of abstractable hydrogen whereby to form a latent image under the influence of said imaging energy.

6. The method of claim 1, in which said imaging energy forms a developable latent image, and then subjecting said latent image to heat and/or reducing sugars to produce a visible image defined by crystalline tellurium advantageously at least mainly in the form of needles.

7. A method for producing an image comprising:
providing a layer including an imaging material in the form of a tellurium tetrahalide adduct of an aromatic amine in which nitrogen attached directly or indirectly to the aromatic radical is substituted by alkyls each containing from 1 to 4 carbon atoms and being free from diazo groups, and a separate spectral sensitizer, applying imaging energy in the form of particle or wave radiation to certain portions of said layer to form a latent image, and then subjecting said latent image to heat and/or reducing sugars to convert said latent image into a developed image defined by crystals of tellurium.

8. The method of claim 7, in which said imaging material corresponds to the formula $((CH_3)_2N\ C_6H_5)_2TeCl_4$.

9. The method of claim 7, in which said imaging material and said spectral sensitizer are dissolved or dispersed in a polymeric matrix material which is at least in part of amorphous character.

10. The method of claim 9, wherein the polymeric matrix material is a polyvinyl formal.

11. The method of claim 6, in which the spectral sensitizer is a polynuclear quinone.

12. The method of claim 7, in which the imaging energy is actinic light and in which the development energy is heat.

13. The method of claim 7, in which the imaging material is sensitive to visible light.

14. The method of claim 7, in which the imaging material is sensitive to ultraviolet light.

15. The method of claim 7, in which the imaging energy is electromagnetic energy and in which the development energy is heat.

16. A method for producing a record of retrievable information comprising:
   (a) providing a layer in the form of a matrix of a glassy, amorphous material which has a glass transition temperature and which carries an imaging material which inherently possesses spectral sensitizer properties and/or is admixed with a separate spectral sensitizer, said imaging material being in the form of a tellurium tetrahalide adduct of an aromatic amine in which nitrogen attached directly or indirectly to the aromatic radical is substituted by alkyls each containing from 1 to 4 carbon atoms and being free from diazo groups, said imaging material being of one structure and having one detectable characteristic which is capable of undergoing a change under the influence of imaging energy to produce a material of different structure having another detectable characteristic,
   (b) selectively applying to said layer imaging energy in the form of particle or wave radiation to form a latent image, with or without the aid of a spectral sensitizer, which latent image is essentially not a record of retrievable information; and developing, through the utilization of heat, either simultaneously with or subsequently to the application of said imaging energy, to produce in the exposed areas an image which is a record of retrievable information constituted by the atoms of the element tellurium.

17. The method of claim 16, in which said energy applied to said layer is electromagnetic energy.

18. The method of claim 17, in which the glassy amorphous material is polyvinyl formal.

19. The method of claim 18, in which the imaging material is a compound of the formula $$((CH_3)_2N\ C_6H_5)_2TeCl_4$$

20. An article for producing a record of retrievable information in the form of a dry-to-the-touch layer comprising an imaging layer including a normally solid polymeric matrix containing an imaging material and a separate spectral sensitizer for the imaging material, said spectral sensitizer being capable of absorbing photons from particle or wave radiation whereby to form a latent image, said imaging material comprising an imaging organo-tellurium material in the form of a tellurium tetrahalide adduct of an aromatic amine in which nitrogen attached directly or indirectly to the aromatic radical is substituted by alkyls each containing from 1 to 4 carbon atoms and being free from diazo groups and being of one structure and having one detectable characteristic and which is capable of undergoing a change in response to the application of imaging energy in the form of particle or wave radiation to produce at the latent image a material of different structure having another detectable characteristic.

21. An article according to claim 20, in which the spectral sensitizer is a polynuclear quinone.

22. The article of claim 21, in which, in the imaging material, the tetrahalide is tetrachloride.

23. The article of claim 22, in which the imaging material is a compound of the formula $((CH_3)_2N\ C_6H_5)_2TeCl_4$.

24. The article of claim 20, in which the spectral sensitizer is 4,5-Pyrenequinone.

25. The article of claim 20, in which the matrix is a polyvinyl formal.

26. The article of claim 20, which contains a small proportion of an organic solvent.

27. The article of claim 20, in which the matrix is a polyvinyl formal, and the spectral sensitizer is 9,10-phenanthrenequinone.

28. The article of claim 26, in which the organic solvent comprises dimethylformamide.

* * * * *